(12) United States Patent
Levine

(10) Patent No.: US 8,398,324 B2
(45) Date of Patent: Mar. 19, 2013

(54) VIAL FOR DELIVERING CONTENTS ONTO A SUBSTRATE

(75) Inventor: Jonathan B. Levine, Purchase, NY (US)

(73) Assignee: JBL Radical Innovations, LLC DE (US)

( * ) Notice: Subject to any disclaimer, the term of this patent is extended or adjusted under 35 U.S.C. 154(b) by 544 days.

(21) Appl. No.: 12/691,766

(22) Filed: Jan. 22, 2010

(65) Prior Publication Data

US 2011/0183296 A1 Jul. 28, 2011

Related U.S. Application Data

(63) Continuation-in-part of application No. 12/407,013, filed on Mar. 19, 2009, now Pat. No. 8,262,306.

(51) Int. Cl.
*B43M 11/06* (2006.01)
(52) U.S. Cl. .............................. 401/183; 433/80; 433/89
(58) Field of Classification Search .......... 401/183–186, 401/145, 152, 156; 222/92, 206, 212; 433/88, 433/89; 604/3, 290
See application file for complete search history.

(56) References Cited

U.S. PATENT DOCUMENTS

| | | | |
|---|---|---|---|
| 3,237,630 A * | 3/1966 | Politzer ........................ 401/37 |
| 3,972,331 A | 8/1976 | Bolduc et al. | |
| 4,279,527 A | 7/1981 | Moe et al. | |
| 4,748,990 A | 6/1988 | Brown et al. | |
| 4,927,283 A | 5/1990 | Fitjer | |
| 5,251,752 A * | 10/1993 | Purohit ........................ 206/352 |
| 5,307,953 A | 5/1994 | Regan | |
| 5,509,744 A | 4/1996 | Frazier | |
| 5,693,313 A | 12/1997 | Shiraishi et al. | |
| 5,857,796 A | 1/1999 | Waldmann | |
| D413,730 S | 9/1999 | Frazier | |
| D416,389 S | 11/1999 | Frazier | |
| 6,254,297 B1 | 7/2001 | Frazier | |
| 6,623,272 B2 | 9/2003 | Clemans | |
| 6,648,904 B2 | 11/2003 | Altshuler et al. | |
| 6,726,482 B2 | 4/2004 | Atkins et al. | |
| 6,755,586 B1 | 6/2004 | Frazier | |
| 6,758,620 B1 * | 7/2004 | Harrold ........................ 401/264 |
| D495,843 S | 9/2004 | Frazier | |
| D504,775 S | 5/2005 | Frazier | |
| 6,902,397 B2 | 6/2005 | Farrell et al. | |
| 6,929,475 B1 | 8/2005 | Dragan | |
| 7,004,657 B2 | 2/2006 | Frazier | |
| 7,004,756 B2 | 2/2006 | Andersen | |
| 7,021,848 B1 | 4/2006 | Gruenbacher et al. | |

(Continued)

OTHER PUBLICATIONS

Carol Lewis, "Fighting Gum Disease: How to Keep Your Teeth" US Food and Drug Admin., FDA Consumer magazine, May-Jun. 2001 pp. 1-9.

(Continued)

*Primary Examiner* — David Walczak
*Assistant Examiner* — Jennifer C Chiang
(74) *Attorney, Agent, or Firm* — H. Jay Spiegel

(57) ABSTRACT

Dispenser for dispensing a substance onto a substrate, such as a tooth treatment compound onto teeth, includes a vial including a pair of thin members forming a cavity therebetween in which the substance is arranged and a conduit defining an internal dispensing channel communicating with the cavity, an applicator tip arranged in connection with the conduit and including projections adapted to contact the substrate, and a cap including a cavity. The cap removably attaches to the vial and when attached, covers the applicator tip and seals the internal channel. When the cap is detached from the vial and the thin members are squeezed toward one another, the substance in the cavity is urged out of the cavity into and through the internal channel in the conduit and onto the projections to enable it to be brought into contact with the substrate.

23 Claims, 3 Drawing Sheets

U.S. PATENT DOCUMENTS

| | | | |
|---|---|---|---|
| 7,070,413 B1 | 7/2006 | Wagner | |
| 7,097,075 B2 * | 8/2006 | Peuker et al. | 222/94 |
| 7,160,111 B2 | 1/2007 | Baughman | |
| 7,201,577 B2 | 4/2007 | Levine | |
| 7,309,185 B2 * | 12/2007 | Thorpe et al. | 401/277 |
| 7,416,358 B2 * | 8/2008 | Legendre | 401/205 |
| 7,435,027 B2 * | 10/2008 | Hetzel | 401/47 |
| 7,465,119 B2 * | 12/2008 | Sogaro | 401/280 |
| 7,597,497 B2 | 10/2009 | Levine | |
| 7,861,897 B2 * | 1/2011 | Sogaro | 222/209 |
| 2002/0021933 A1 * | 2/2002 | Knieriemen | 401/202 |
| 2003/0147684 A1 * | 8/2003 | Hung | 401/26 |
| 2003/0198918 A1 | 10/2003 | Dragan et al. | |
| 2005/0047848 A1 * | 3/2005 | Carraher | 401/266 |
| 2006/0008316 A1 * | 1/2006 | Greer et al. | 401/202 |
| 2007/0020028 A1 | 1/2007 | Levine | |
| 2007/0116509 A1 * | 5/2007 | Lin | 401/266 |
| 2007/0122769 A1 | 5/2007 | Levine | |
| 2007/0166666 A1 | 7/2007 | Levine | |
| 2007/0183988 A1 | 8/2007 | Prosise et al. | |
| 2008/0245380 A1 * | 10/2008 | Ecker et al. | 132/114 |
| 2009/0152267 A1 | 6/2009 | May et al. | |

OTHER PUBLICATIONS

Kleber, CJ dt al "In vitro tooth whitening by a sodium bicarbonate/peroxide dentifrice" (J. Clin Dent. 1998), pp. 1-2.

* cited by examiner

VIAL FOR DELIVERING CONTENTS ONTO A SUBSTRATE

RELATED US APPLICATION DATA

This application is a continuation-in-part of U.S. patent application Ser. No. 12/407,013 filed Mar. 19, 2009 now U.S. Pat. No. 8,262,306.

FIELD OF THE INVENTION

The present invention relates generally to a vial suited to deliver a dispensable substance onto a substrate, such as an anatomical part, and methods for applying a substance from such a vial onto a substrate, such as an anatomical part.

The present invention relates more specifically, to a vial suited to deliver substances onto teeth and methods for treating teeth. Dental treatments that can be performed using the vial include, but are not limited to, whitening teeth, desensitizing teeth, and treating teeth to prevent periodontal disease.

BACKGROUND OF THE INVENTION

The delivery of topical medicine from a vial to skin to treat skin conditions or to penetrate the skin for medicinal purposes is known. Likewise, the delivery of tooth whitener gel compositions from a vial is known.

For example, U.S. Pat. No. 7,201,577 discloses a tooth whitener applicator and method. The applicator is a conventional glass ampoule having a tooth whitening solution vacuum-sealed within a chamber of the ampoule. The whitening solution is a liquid based gel containing a whitening formula.

Further, U.S. Pat. No. 7,597,497 discloses a dispenser and applicator for liquid, such as a tooth whitening composition, including a container having an internal chamber and an opening initially sealed by a seal such that liquid within the chamber is hermetically sealed therein, a porous applicator mounted on the container above the opening and overlying the seal, and an over-cap covering the applicator and opening and which is movable with respect to the container and carries a piercing member. The over-cap is movable from a position at which the piercing member is spaced from the seal to a position at which the piercing member extends through the applicator and pierces the seal. The porous applicator includes an opening sized to receive the piercing member. The piercing member is disposed in the opening when the piercing member is spaced from the seal, and the porous applicator is formed of a material having a sufficiently high density that the opening narrows when the piercing member is removed from the opening, to preclude free flow of liquid through the opening.

Additional prior art relating to hand-held dispenser of tooth whitening composition or other dispensable substances include U.S. Published Patent Application No. 2003/0198918, and U.S. Pat. Nos. 3,972,331, 4,927,283 and 5,307,953.

SUMMARY OF THE INVENTION

One aspect of the invention resides in a flexible plastic vial. One end of the vial is preferably closed and the other preferably plugged. The plugged end opens as a plug is pulled out. This allows the contents of the vial to be squeezed and poured out through a channel to reach an applicator.

There is a mating structure that closes the open end of the flexible vial in a retracted relative position and that opens the open end of the flexible vial in a cleared relative position. The vial is partly flexible to narrow an interior volume under manual squeezing pressure so that when the open end of the vial is open and no longer plugged by the mating structure, contents (such as a gel) within the interior of the vial are urged out of the interior volume to pass though the channel in the applicator tip as the flexible portion of the vial is flexed under the manual squeezing pressure.

The squeezing of the flexible plastic vial narrows the interior accordingly, which tends to urge the contents, such as the tooth whitening composition gel, toward the path of least resistance—toward the open end to pass through the channel in the applicator tip. Further, by pointing the applicator tip downward and thereby the open end of the vial, gravity will assist in urging the contents, such as the tooth whitening composition gel, toward the open end.

The contents of the flexible vial may be a tooth whitening composition gel of any desired viscosity, including those of relatively high viscosities so as to better adhere to teeth surfaces to be whitened than would otherwise be the case for tooth whitening compositions of lesser viscosity. For applications other than dentistry in which the contents are delivered to a surface of a tooth, the contents may be delivered to other areas of the body. That also needs the formulary to be in a hermetically sealed environment. For instance, a pharmaceutical application would deliver a topical medicine or emollient to a skin surface for treatment of a medical malady, such as skin diseases, burns and other applications such as those requiring the pharmaceutical to penetrate through pores in the skin and the formulation needs to be in a hermetically sealed chamber for stability purposes. In other applications, the contents could be an alternative medicine remedy, herbal extract or other medicinal remedy, or be used to color the skin and/or for cosmetic purposes.

The present invention, therefore, addresses the need for applying relatively small portions of gel to an area to be treated, such as a tooth surface, even providing easy access to rear teeth without the need to place fingers in the mouth. Indeed, the present invention fulfills the need to provide an airtight seal of the vial contents and enable reseal the vial contents in a manner that is equally airtight. The present invention also enables even spreading of the gel onto an area to be treated, such as a tooth surface. The present invention also dispenses the product contents of the vial in a manner such that little unused product contents remain after exhausting the manual squeezing of the flexible portion of the vial. The present invention may be easily manufactured and filled at relatively high production rates.

BRIEF DESCRIPTION OF THE DRAWINGS

For a better understanding of the present invention, reference is made to the following description and accompanying drawings, while the scope of the invention is set forth in the appended claims:

DETAILED DESCRIPTION OF PREFERRED EMBODIMENTS

Figure 1:
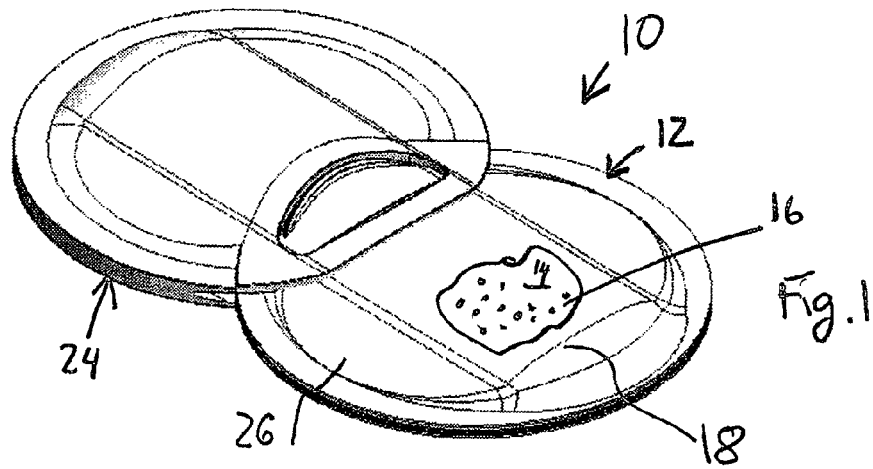
FIG. 1 is an isometric view of a dispenser in accordance with the invention, partly broken away to show an interior.
Figure 3:
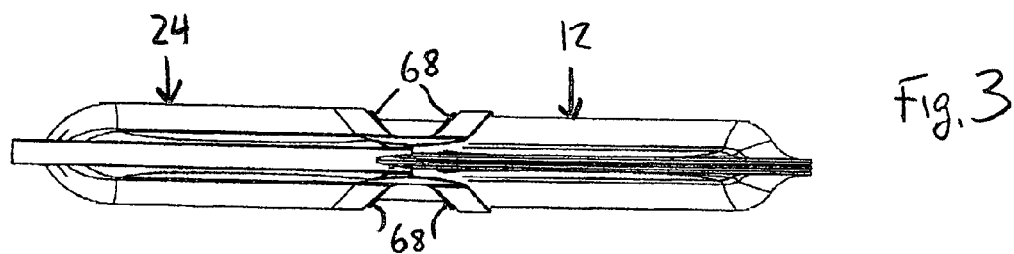
FIG. 3 is a side view of the dispenser in accordance with the invention.

Referring now to the accompanying drawings wherein the same reference numerals refer to the same or similar elements, FIG. 1 shows a perspective view of a dispenser 10 in accordance with the invention that may be used to dispense any type of substance onto a substrate. Possible substances for dispensing onto a substrate include, but are not limited to, dispensing of toothpaste or dentifrice onto teeth, dispensing of whitening gel onto teeth, dispensing of a tooth desensitizing material onto teeth, dispensing of a topical compound to skin, dispensing of a pharmaceutical skin product to skin, and dispensing of adhesive onto a surface to be adhered to something else.

Dispenser 10 generally includes a vial 12 having a cavity 14 in which the substance 16 is contained and a squeezable portion 18 that when squeezed, urges the substance 16 out of the cavity 14 into an internal, dispensing channel 20, an applicator tip 22 onto which the substance 16 is urged and which can be brought into contact with the substrate, and a cap 24 that removably attaches to the vial 12 and closes the dispensing channel 20.

More particularly, the vial 12 has a substantially circular portion 26 and a conduit 28 extending outward from the circular portion 26, and which defines part of the internal channel 20. Conduit 28 has a substantially oval cross-sectional shape. Circular portion 26 includes a support portion 30 along a partial circumferential edge of the circular portion 26, and an arcuate support rim 32 connected to opposite sides of the support portion 30 and extending over the remaining circumferential edge of the circular portion 26 to thereby complete the circular form of circular portion 26. A remaining part of the internal channel 20 is defined in the support portion 30. Cross supports 34 extend from the support portion to opposite inner edges of the support rim 32 and thereby define open areas 36, 38, 40 between the support portion 30, the support rim 32 and the cross supports 34.

As shown, the internal channel 20 has a particular cross sectional shape with larger horizontal legs 42 than vertical legs 44. However, the cross-sectional shape of the internal channel 20 may vary, subject only to the requirement that it easily enable a flow of the substance in the cavity 14 therethrough upon application of pressure to opposed surfaces of the squeezable portion 18 of the vial 12.

Circular portion 26 of the vial 12 also includes a pair of partially flexible members 46 each arranged on a respective side of the support rim 32 and attached to the support portion 30 and/or support rim 32 to form the cavity 14. Cavity 14 is thus formed between inner surfaces of the members 46 and between the cross supports 34.

Each member 46 has a shape substantially conforming to a shape of the support rim 32, when viewed from above, i.e., generally crescent-shaped. Thus, when attached to the support portion 30 and/or support rim 32, the members 46 can lie substantially flush with the support portion 30 without any gap therebetween. Moreover, each member 46 has first and second flange portions 48 that are substantially planar and an arcuate portion 50 therebetween extending outward from a plane in which the flange portions 48 are arranged (see FIG. 4). When attached to the support portion 30 and/or support rim 32, the first and second flange portions 48 are each arranged between a respective cross support 34 and an adjacent portion of the support rim 32, and the arcuate portion 50 is arranged between the cross supports 34 and extends outward.

The arcuate portions 50 of the members 46 are flexible or otherwise constructed to be squeezable toward one another so that when squeezed, the substance 16 can be urged out of the cavity 14 and into and through the internal channel 20 in communication therewith. Members 46 preferably contact the cross supports 34 to thereby prevent flow of the substance 16 from the cavity 14 around the cross supports 34 into the flange areas of the circular portion 26 of the vial 12 defined between the flange portions 48 of the members 46.

Figure 4:
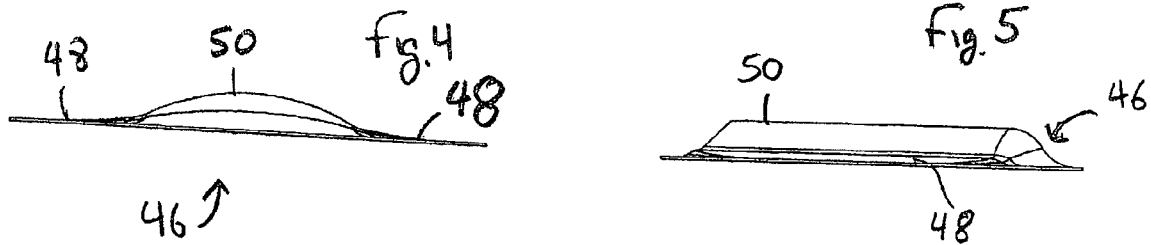
FIG. 4 is a front view of a thin member of the vial of the dispenser in accordance with the invention.
Figure 5:
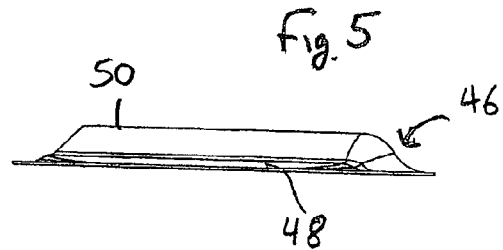
FIG. 5 is a front view of a thin member of the vial of the dispenser in accordance with the invention.

The members 46 provide the circular portion 26 of the vial 12 with opposed substantially circular surfaces that are variably spaced apart from one another, i.e., a smaller spacing in the areas of flange portions 48 than arcuate portions 50, and form the cavity 14 between opposed portions of the circular surfaces. Moreover, the circular surfaces have an undulating form with low points at lateral edges of the circular portion 26 (i.e., at the edges of the flange portions 48) and a high point in a center of the circular portion (i.e., at the center of the arcuate portion 50), as shown in FIG. 4. The circular surfaces gently slope between the low points and the high point.

The applicator tip 22 is elongate and arranged over the conduit 28, and to provide a tight fit over conduit 28, the applicator tip 22 may have substantially the same cross-sectional shape as the conduit 28, i.e., oval as shown. A distal end of the applicator tip 22 includes projections 52 that are adapted to contact the substrate. The applicator tip 22 may be overmolded onto the conduit 28 such that a portion of the applicator tip 22 including the projections 52 extends beyond an axial edge of the conduit 28.

Figure 8:
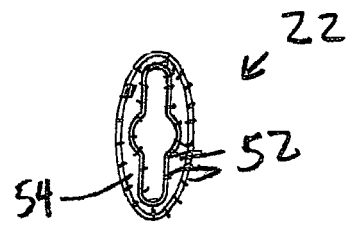
FIG. 8 is a front view of an applicator tip of the dispenser in accordance with the invention

Projections 52 may be in the form of crenellated fingers arranged to provide an even spreading of the substance 16 onto the substrate, see FIG. 8. The crenellated fingers may be arranged to form two or more oval or annular rows, each pair of adjacent rows being separated by a channel 54. The projections 52 and channel 54 cooperate to define retention areas in which the substance 16 is retained ready for application to the substrate.

Figure 6:
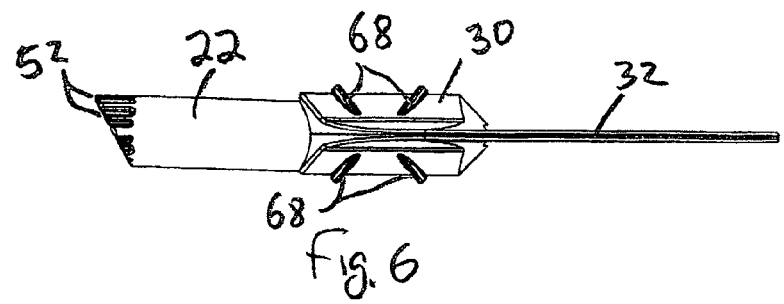
FIG. 6 is a side view of part of the dispenser in accordance with the invention.

In a preferred embodiment shown in FIG. 6, the projections 52 have a variable axial length from a largest axial length on one side of the applicator tip 22 to a shortest axial length on an opposite side of the applicator tip 22.

Figure 9:
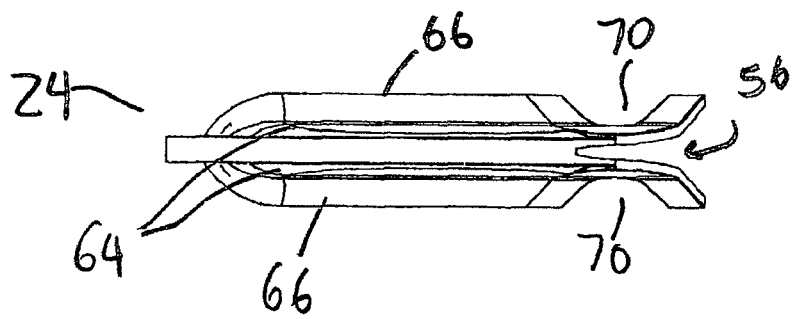
FIG. 9 is a front view of a cap of the dispenser in accordance with the invention.
Figure 10:
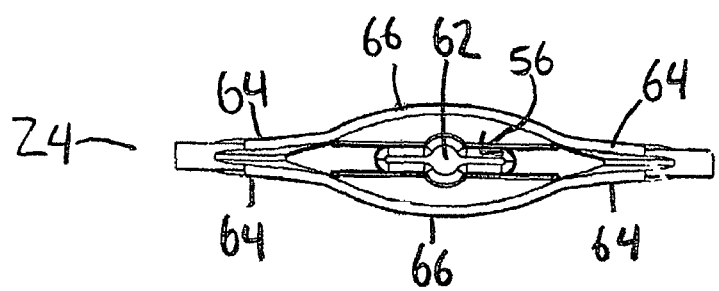
FIG. 10 is a side view of the cap of the dispenser in accordance with the invention.
Figure 11:
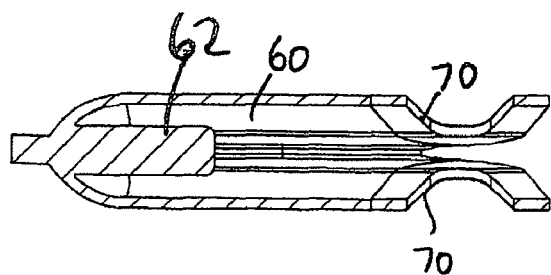
FIG. 11 is a cross-section of the cap of FIG. 9 taken along the line 11-11 in FIG. 2.

Referring now to FIGS. 9-11, the cap 24 includes an opening 56 on an inner side leading into a cavity 60 and which is arranged to accommodate the exposed portion of the applicator tip 22, and a sealing stopper 62 that enters into the internal channel 20 when the cap 24 is attached to the vial 12 to thereby seal the internal channel 20.

Cap 24 is substantially circular such that when attached to the vial 12 and covering the applicator tip 22, the dispenser 10 has the form of the number eight. Moreover, the cap 24 may have a form similar to that of the circular portion 26, i.e., flange portions 64 and an arcuate portion 66 therebetween extending outward from a plane in which the flange portions 64 are arranged.

The support portion 26 and the cap 24 include a cooperating securing mechanism for releasably securing the cap to the vial 12.

Figure 2:
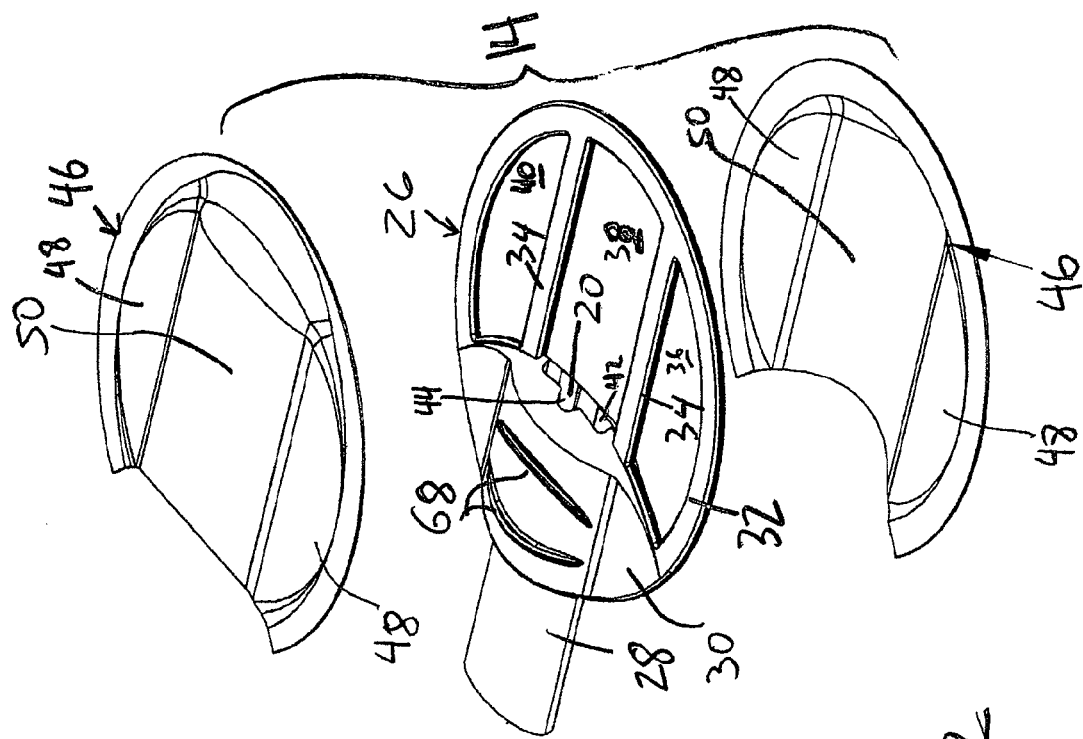
FIG. 2 is an exploded isometric view of the dispenser in accordance with the invention.
Figure 2:
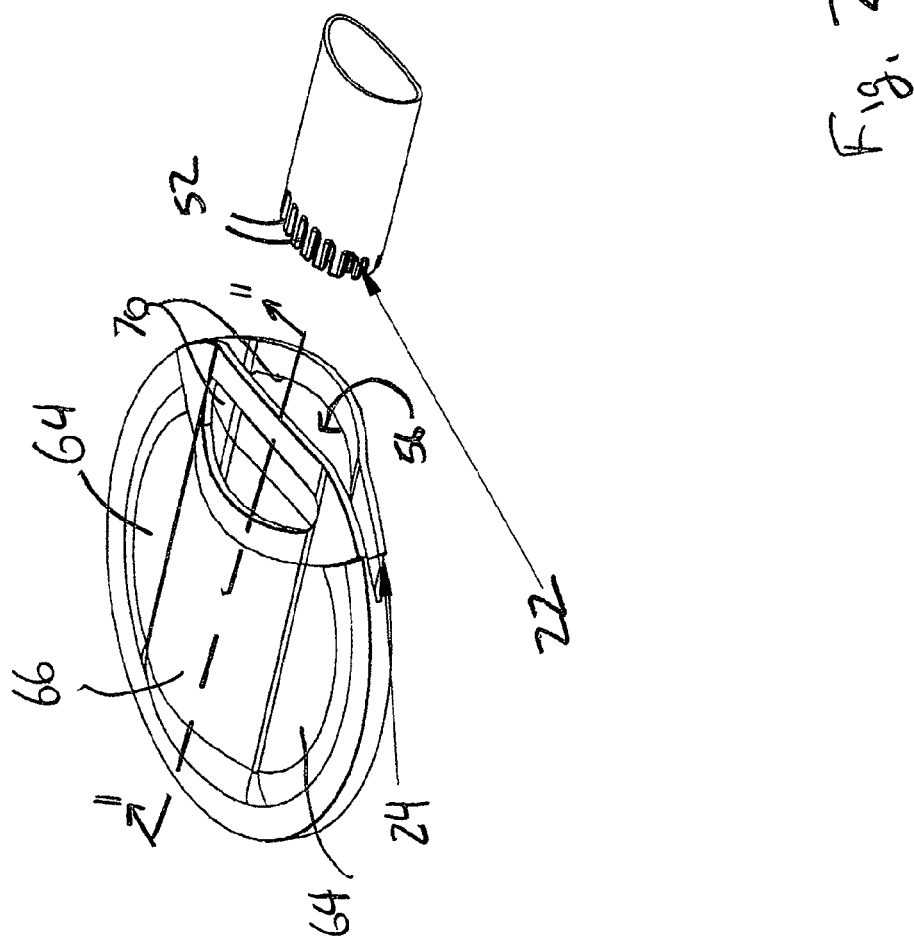
Figure 7:
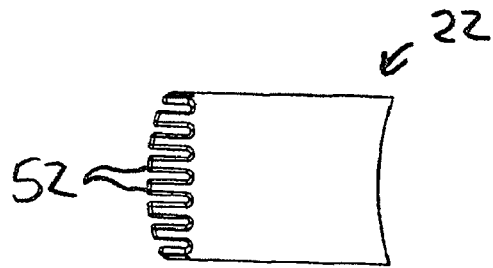
FIG. 7 is a top view of an applicator tip of the dispenser in accordance with the invention

As shown in FIG. 2, the securing mechanism includes ridges 68 formed on opposed upper and lower surfaces of the circular portion 26 and apertures 70 formed on the cap 24 to receive the ridges 68. In one embodiment, at a minimum, the securing mechanism includes a ridge on the circular portion 26 of the vial 12 and an abutting surface on a portion of the cap 24 that is positioned to abut against a rear facing surface of the ridge 68 to thereby prevent rearward movement of the vial 12 relative to the cap 24 and thus disengagement of the vial 12 and cap 24 from one another, in the absence of manual force urging the ridge 68 under the abutting surface.

Various materials may be used to form the components described above. For example, the circular portion 26 of the vial 12 may be made of high density polyethylene (HDPE), the members 46 may be made of film or foil, the applicator tip may be made of a soft material such as silicone.

While the foregoing description and drawings represent the preferred embodiments of the present invention, it will be understood that various changes and modifications may be made without departing from the scope of the present invention.

The invention claimed is:

1. A dispenser for dispensing a substance onto a substrate, comprising:
   a vial including a pair of thin, outwardly bulging partly flexible convex members each arranged on a respective side of said vial and forming a narrow cavity therebetween in which the substance is stored and a conduit defining an internal dispensing channel communicating with said cavity, said thin members being partly squeezable toward one another;
   an applicator tip connected with said conduit and including projections adapted to contact the substrate; and
   a cap including a cavity, said cap being removably attached to said vial and when attached to said vial, covering said applicator tip and sealing said internal dispensing channel,
   whereby when said cap is removed from said vial and said thin members are squeezed toward one another, the substance in said cavity is urged out of said cavity through said internal dispensing channel in said conduit and onto said projections to be brought into contact with the substrate.

2. The dispenser of claim 1, wherein said vial is substantially circular and includes an annular rim, a support portion along a portion of said rim, a pair of supports each extending between said support portion and an opposite portion of said rim, said cavity being defined between said supports, said conduit being situated partially within said support portion.

3. The dispenser of claim 2, wherein said thin members each have a shape conforming to a shape of said rim aside from said support portion.

4. The dispenser of claim 2, wherein said thin members each have first and second substantially planar portions and a convex portion therebetween extending outward from a plane in which said planar portions are arranged, said arcuate portions of said thin members being flexible and thus squeezable toward one another to thereby urge the substance out of said cavity.

5. The dispenser of claim 2, wherein said rim, said support portion and said supports are made of high density polyethylene.

6. The dispenser of claim 1, wherein said applicator tip is overmolded onto said conduit such that a portion of said applicator tip including said projections extends beyond an axial edge of said conduit.

7. The dispenser of claim 1, wherein said projections comprise crenellated fingers arranged to provide an even spreading of the substance onto the substrate.

8. The dispenser of claim 7, wherein said crenellated fingers form a plurality of annular rows, each pair of adjacent rows being separated by a channel, said fingers and said channel cooperating to define retention areas in which the substance is retained ready for application to the substrate.

9. The dispenser of claim 1, wherein said applicator tip is made of a soft material such as silicone.

10. The dispenser of claim 1, wherein said applicator tip is elongate and said projections comprise inner and outer rings of projections separated by a channel, said projections having a variable axial length from a largest axial length on one side of said applicator tip to a shortest axial length on an opposite side of said applicator tip.

11. The dispenser of claim 1, wherein said thin members are made of film or foil.

12. The dispenser of claim 1, wherein said cap includes an opening on an inner side for receiving said applicator tip and a sealing stopper for entering into said internal channel when said cap is attached to said vial.

13. The dispenser of claim 1, wherein said cap is configured such that when said cap is attached to said vial, said dispenser has the form of the number eight.

14. The dispenser of claim 1, wherein said cap includes a securing mechanism for releasably securing said cap to said vial.

15. The dispenser of claim 14, wherein said vial includes at least one ridge formed on an outer surface at a front area, said securing mechanism comprising a respective abutting surface of a portion of said cap that is positioned to abut against a rear facing surface of each of said at least one ridge to thereby prevent rearward movement of said vial relative to said cap, and thus disengagement of said vial and cap from one another, in the absence of manual force urging said ridge under said respective abutting surface.

16. A dispenser for dispensing a substance onto a substrate, comprising:
   a vial comprising a substantially circular portion having a cavity therein containing the substance and a conduit extending outward from said circular portion and defining an internal channel communicating with said cavity, said vial having opposed substantially circular convex surfaces variably spaced apart from one another to enable formation of said cavity between opposed portions of said circular surfaces;
   an applicator tip arranged in connection with said conduit and adapted to contact the substrate; and
   a cap including a sealing stopper, said cap being removably attached to said vial such that when said cap is attached to said vial, said sealing stopper said cap covers said applicator tip and seals said internal channel,
   whereby when said cap is removed from said vial and said circular surfaces are squeezed toward one another, the substance in said cavity is urged out of said cavity through said internal channel in said conduit to be brought into contact with the substrate.

17. The dispenser of claim 16, wherein said circular surfaces have an undulating form with low points at lateral edges of said circular portion and a high point in a center of said circular portion, said circular surfaces gently sloping between said low points and said high point.

18. A dispenser for dispensing a substance onto a substrate, comprising:
   a vial comprising a cavity containing the substance and a conduit defining an internal channel communicating with said cavity, said vial having opposed surfaces squeezable toward one another;

an applicator tip arranged in connection with said conduit and adapted to contact the substrate; and a cap including a sealing stopper, said cap being removably attached to said vial such that when said cap is attached to said vial, said sealing stopper said cap covers said applicator tip and seals said internal channel, said cap being configured such that when said cap is attached to said vial, said dispenser has the form of the number, eight with said vial comprising a first loop of said number eight and said cap comprising a second loop of said number eight;

whereby when said cap is removed from said vial and said opposed surfaces of said vial are squeezed toward one another, the substance in said cavity is urged out of said cavity through said internal channel in said conduit to be brought into contact with the substrate.

19. The dispenser of claim 18, wherein said cap is substantially crescent-shaped and includes an opening on an inner side for receiving said applicator tip.

20. A dispenser for dispensing a substance onto a substrate, comprising:

a vial including a pair of thin, partly flexible members each arranged on a respective side of said vial and forming a cavity therebetween in which the substance is arranged and a conduit defining an internal dispensing channel communicating with said cavity, said thin members being partly squeezable toward one another;

said vial being substantially circular and including an annular rim, a support portion located along a portion of said rim, a pair of supports each extending between said support portion and an opposite portion of said rim, said cavity being defined between said supports, said conduit being situated partially within said support portion;

an applicator tip arranged in connection with said conduit and including projections adapted to contact the substrate; and a cap including a cavity, said cap being removably attached to said vial and when attached to said vial, covering said applicator tip and sealing said internal channel, whereby when said cap is removed from said vial and said thin members are squeezed toward one another, the substance in said cavity is urged out of said cavity through said internal channel in said conduit and onto said projections to be brought into contact with the substrate.

21. A dispenser for dispensing a substance onto a substrate, comprising:

a vial including a pair of thin, partly flexible members each arranged on a respective side of said vial and forming a cavity therebetween in which the substance is arranged and a conduit defining an internal dispensing channel communicating with said cavity, said thin members being partly squeezable toward one another;

an applicator tip arranged in connection with said conduit and including projections adapted to contact the substrate, said projections comprising crenellated fingers arranged to provide an even spreading of the substance onto the substrate; and a cap including a cavity, said cap being removably attached to said vial and when attached to said vial, covering said applicator tip and sealing said internal channel, whereby when said cap is removed from said vial and said thin members are squeezed toward one another, the substance in said cavity is urged out of said cavity through said internal channel in said conduit and onto said projections to be brought into contact with the substrate.

22. A dispenser for dispensing a substance onto a substrate, comprising:

a vial including a pair of thin, partly flexible members each arranged on a respective side of said vial and forming a cavity therebetween in which the substance is arranged and a conduit defining an internal dispensing channel communicating with said cavity, said thin members being partly squeezable toward one another;

an elongated applicator tip arranged in connection with said conduit and including projections adapted to contact the substrate, said projections comprising inner and outer rings of projections separated by a channel, said projections having a variable axial length from a largest axial length on one side of said applicator tip to a shortest axial length on an opposite side of said applicator tip; and a cap including a cavity, said cap being removably attached to said vial and when attached to said vial, covering said applicator tip and sealing said internal channel, whereby when said cap is removed from said vial and said thin members are squeezed toward one another, the substance in said cavity is urged out of said cavity through said internal channel in said conduit and onto said projections to be brought into contact with the substrate.

23. A dispenser for dispensing a substance onto a substrate, comprising:

a vial including a pair of thin, partly flexible members each arranged on a respective side of said vial and forming a cavity therebetween in which the substance is arranged and a conduit defining an internal dispensing channel communicating with said cavity, said thin members being partly squeezable toward one another;

an applicator tip arranged in connection with said conduit and including projections adapted to contact the substrate; and a cap including a cavity, said cap being removably attached to said vial and when attached to said vial, covering said applicator tip and sealing said internal channel, said cap including a securing mechanism for releasably securing said cap to said vial, whereby when said cap is removed from said vial and said thin members are squeezed toward one another, the substance in said cavity is urged out of said cavity through said internal channel in said conduit and onto said projections to be brought into contact with the substrate, said vial including at least one ridge formed on an outer surface at a front area thereof, said securing mechanism comprising a respective abutting surface of a portion of said cap that is positioned to abut against a rear facing surface of each of said at least one ridge to thereby prevent rearward movement of said vial relative to said cap and disengagement of said vial and cap from one another, in the absence of manual force urging said ridge under said respective abutting surface.

* * * * *